(12) United States Patent
Park et al.

(10) Patent No.: US 12,102,826 B2
(45) Date of Patent: Oct. 1, 2024

(54) SYSTEMS AND METHODS FOR GENERATING PULSED WAVEFORMS THAT APPROXIMATE COLORED NOISE

(71) Applicant: Advanced Neuromodulation Systems, Inc., Plano, TX (US)

(72) Inventors: Hyun-Joo Park, Frisco, TX (US); Simeng Zhang, Frisco, TX (US); Yagna Pathak, Skokie, IL (US); Erika Ross, Dallas, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 170 days.

(21) Appl. No.: 17/082,318

(22) Filed: Oct. 28, 2020

(65) Prior Publication Data

US 2022/0080202 A1 Mar. 17, 2022

Related U.S. Application Data

(60) Provisional application No. 63/077,079, filed on Sep. 11, 2020.

(51) Int. Cl.
*A61N 1/36* (2006.01)
*A61N 1/02* (2006.01)
(Continued)

(52) U.S. Cl.
CPC ......... *A61N 1/36125* (2013.01); *A61N 1/025* (2013.01); *A61N 1/36192* (2013.01);
(Continued)

(58) Field of Classification Search
CPC .............. A61N 1/36125; A61N 1/025; A61N 1/36192; A61N 1/36196; A61N 1/0534;
(Continued)

(56) References Cited

U.S. PATENT DOCUMENTS 3,614,783 A * 10/1971 Adrian .................. G01S 13/347
102/214
7,212,110 B1 5/2007 Martin et al.
(Continued)

FOREIGN PATENT DOCUMENTS

WO 2001093953 A1 12/2001
WO 2020099921 A3 5/2020

OTHER PUBLICATIONS

International Search Report and Written Opinion, PCT/US2021/049752, mailing date: Jan. 5, 2022, 15 pages.

*Primary Examiner* — Gary Jackson
*Assistant Examiner* — Alexander M Eisenberg
(74) *Attorney, Agent, or Firm* — Armstrong Teasdale LLP (57) ABSTRACT

The present disclosure provides systems and methods for generating pulsed waveforms that approximate colored noise for use in a neurostimulation system. An implantable neurostimulation system includes an implantable stimulation lead including a plurality of contacts, and an implantable pulse generator communicatively coupled to the stimulation lead. The pulse generator is configured to generate a pulsed waveform that approximates colored noise using at least one of a thresholding method and an optimization method, and cause stimulation to be delivered by the stimulation lead based on the pulsed waveform.

10 Claims, 5 Drawing Sheets

(51) Int. Cl.
*A61N 1/05* (2006.01)
*G16H 20/30* (2018.01)

(52) U.S. Cl.
CPC ......... *A61N 1/36196* (2013.01); *G16H 20/30* (2018.01); *A61N 1/0534* (2013.01); *A61N 1/0551* (2013.01); *A61N 1/3616* (2013.01)

(58) Field of Classification Search
CPC ................ A61N 1/0551; A61N 1/3616; A61N 1/36171; A61N 1/36082; A61N 1/36175; A61N 1/0553; A61N 1/36067; A61N 1/36071
See application file for complete search history.

(56) References Cited

U.S. PATENT DOCUMENTS

| | | |
|---|---|---|
| 7,228,179 B2 | 6/2007 | Campen et al. |
| 7,571,007 B2 | 8/2009 | Erickson et al. |
| 9,314,190 B1* | 4/2016 | Giuffrida .............. A61M 5/1723 |
| 2002/0172261 A1* | 11/2002 | Hershey ................... H04B 1/71 |
| | | 375/147 |
| 2006/0170486 A1 | 8/2006 | Tranchina et al. |
| 2010/0106231 A1* | 4/2010 | Torgerson .......... A61N 1/36082 |
| | | 607/116 |
| 2012/0059438 A1 | 3/2012 | De Ridder |
| 2012/0259382 A1* | 10/2012 | Trier .................. A61N 1/36071 |
| | | 607/46 |
| 2015/0157864 A1 | 6/2015 | Rosenberg |
| 2015/0290460 A1* | 10/2015 | De Ridder ......... A61N 1/36146 |
| | | 607/45 |
| 2018/0001088 A1* | 1/2018 | Tass ..................... A61N 5/0622 |
| 2018/0169372 A1* | 6/2018 | Bornzin ............... A61N 1/3606 |
| 2018/0185645 A1* | 7/2018 | Vallejo ............... A61N 1/36171 |
| 2019/0329040 A1* | 10/2019 | Mustakos .......... A61N 1/36182 |
| 2019/0366107 A1* | 12/2019 | Moffitt ............... A61N 1/36185 |

\* cited by examiner

SYSTEMS AND METHODS FOR GENERATING PULSED WAVEFORMS THAT APPROXIMATE COLORED NOISE

CROSS REFERENCE TO RELATED APPLICATIONS

This application claims priority to provisional application Ser. No. 63/077,079, filed Sep. 11, 2020, which is incorporated herein by reference in its entirety.

FIELD OF THE DISCLOSURE

The present disclosure relates generally to neurostimulation systems, and more particularly to generated pulsed waveforms that approximate colored noise.

BACKGROUND ART

Neurostimulation is an established neuromodulation therapy for the treatment of chronic pain and movement disorders. For example, neurostimulation has been shown to improve cardinal motor symptoms of Parkinson's Disease (PD), such as bradykinesia, rigidity, and tremors. Types of neurostimulation include deep brain stimulation (DBS), spinal cord stimulation (SCS), and Dorsal Root Ganglion (DRG) stimulation.

Electrophysiology recordings from the brain indicate that, for background noise signals in the brain, the power in the frequency domain follows that of pink noise ($1/f$) to brown noise ($1/f^2$). The background noise has also been shown to be task and age dependent, suggesting that the noise is a physiological signal. Accordingly, playing back recorded colored noise to the brain or neural tissue has been suggested as a potential neuromodulation technique.

However, because the power of this colored noise is primarily located in low frequency components, the time domain representation is characterized with a slow, varying profile. As a result, these colored noise waveforms have a long duration of anodic or cathodic phases before switching polarity. In electrode-tissue interfaces, the long phase duration may, in some scenarios, be detrimental to tissue, due to the accumulation of substances as a result of irreversible Faraday reactions at the interface or due to electrode corrosion by oxidation of metallic electrodes. Therefore, in electric stimulation of excitable tissue, charge balanced or slightly imbalanced biphasic waveforms are typically used to avoid irreversible Faraday reactions.

Accordingly, it would be desirable to provide stimulation waveforms that maintain a power spectral density similar to colored nose, while avoiding relatively long anodic or cathodic phases.

BRIEF SUMMARY OF THE DISCLOSURE

In one embodiment, the present disclosure is directed to an implantable neurostimulation system. The neurostimulation system includes an implantable stimulation lead including a plurality of contacts, and an implantable pulse generator communicatively coupled to the stimulation lead and configured to generate a pulsed waveform that approximates colored noise using at least one of a thresholding method and an optimization method, and cause stimulation to be delivered by the stimulation lead based on the pulsed waveform.

In another embodiment, the present disclosure is directed to an implantable pulse generator. The pulse generator includes a memory device, and a processor coupled to the memory device, the processor configured to generate a pulsed waveform that approximates colored noise using at least one of a thresholding method and an optimization method.

In another embodiment, the present disclosure is directed to a method of applying neurostimulation. The method includes generating, using an implantable pulse generator, a pulsed waveform that approximates colored noise using at least one of a thresholding method and an optimization method, and applying the waveform to a patient using an implantable stimulation lead coupled to the pulse generator.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The present disclosure provides systems and methods for generating pulsed waveforms that approximate colored noise for use in a neurostimulation system. An implantable neurostimulation system includes an implantable stimulation lead including a plurality of contacts, and an implantable pulse generator communicatively coupled to the stimulation lead. The pulse generator is configured to generate a pulsed waveform that approximates colored noise using at least one of a thresholding method and an optimization method, and cause stimulation to be delivered by the stimulation lead based on the pulsed waveform.

Neurostimulation systems are devices that generate electrical pulses and deliver the pulses to nervous tissue of a patient to treat a variety of disorders. One category of neurostimulation systems is deep brain stimulation (DBS). In DBS, pulses of electrical current are delivered to target regions of a subject's brain, for example, for the treatment of movement and effective disorders such as Parkinson's Disease (PD) and essential tremor. Another category of neurostimulation systems is spinal cord stimulation (SCS) which is often used to treat chronic pain such as Failed Back Surgery Syndrome (FBSS) and Complex Regional Pain Syndrome (CRPS).

Neurostimulation systems generally include a pulse generator and one or more leads. A stimulation lead includes a lead body of insulative material that encloses wire conductors. The distal end of the stimulation lead includes multiple electrodes, or contacts, that intimately impinge upon patient tissue and are electrically coupled to the wire conductors. The proximal end of the lead body includes multiple terminals (also electrically coupled to the wire conductors) that are adapted to receive electrical pulses. In DBS systems, the distal end of the stimulation lead is implanted within the brain tissue to deliver the electrical pulses. The stimulation leads are then tunneled to another location within the patient's body to be electrically connected with a pulse generator or, alternatively, to an "extension." The pulse generator is typically implanted in the patient within a subcutaneous pocket created during the implantation procedure.

The pulse generator is typically implemented using a metallic housing (or can) that encloses circuitry for generating the electrical stimulation pulses, control circuitry, communication circuitry, a rechargeable or primary cell battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on the proximal end of a stimulation lead.

Figure 1:
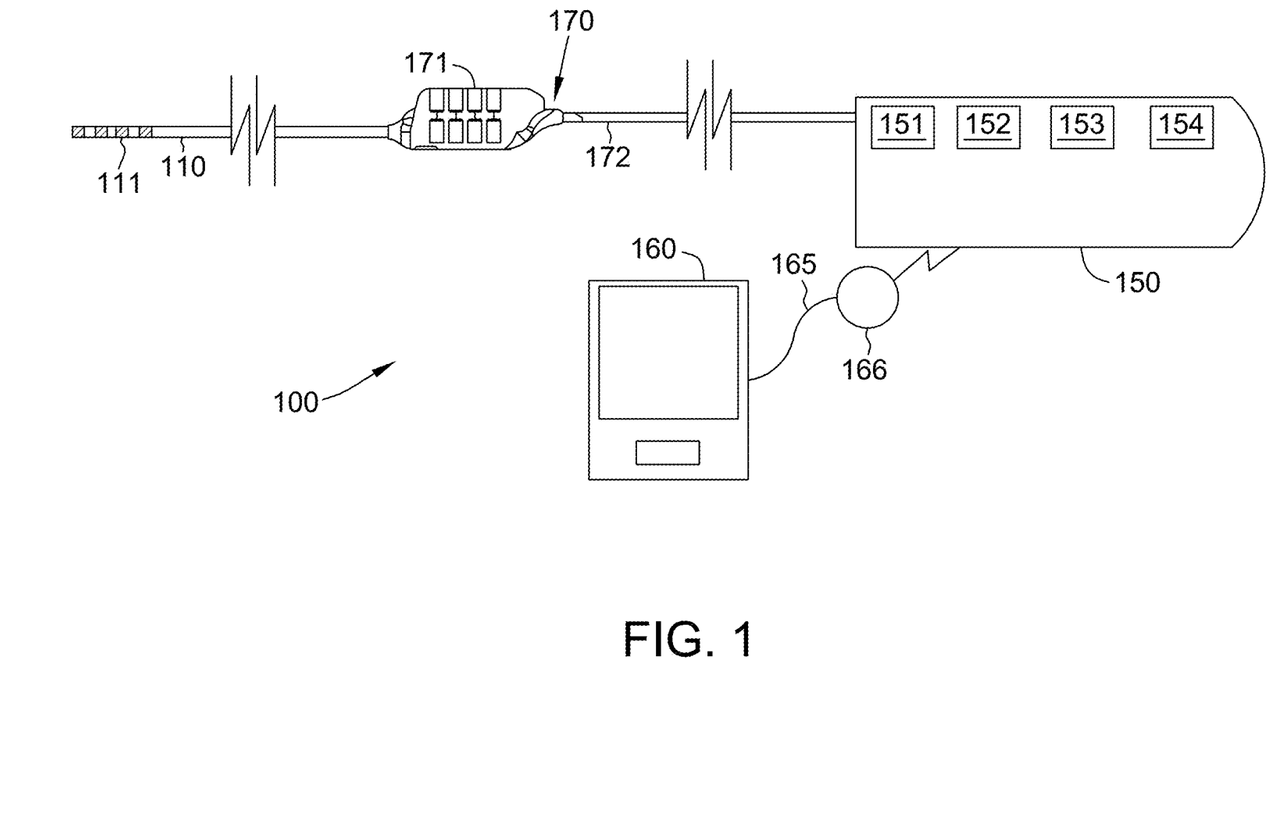
FIG. 1 is a schematic view of one embodiment of a stimulation system.

Referring now to the drawings, and in particular to FIG. 1, a stimulation system is indicated generally at 100. Stimulation system 100 generates electrical pulses for application to tissue of a patient, or subject, according to one embodiment. System 100 includes an implantable pulse generator (IPG) 150 that is adapted to generate electrical pulses for application to tissue of a patient. Alternatively, system 100 may include an external pulse generator (EPG) positioned outside the patient's body. IPG 150 typically includes a metallic housing (or can) that encloses a controller 151, pulse generating circuitry 152, a battery 153, far-field and/or near field communication circuitry 154, and other appropriate circuitry and components of the device. Controller 151 typically includes a microcontroller or other suitable processor for controlling the various other components of the device. Software code is typically stored in memory of IPG 150 for execution by the microcontroller or processor to control the various components of the device.

IPG 150 may comprise one or more attached extension components 170 or be connected to one or more separate extension components 170. Alternatively, one or more stimulation leads 110 may be connected directly to IPG 150. Within IPG 150, electrical pulses are generated by pulse generating circuitry 152 and are provided to switching circuitry. The switching circuit connects to output wires, traces, lines, or the like (not shown) which are, in turn, electrically coupled to internal conductive wires (not shown) of a lead body 172 of extension component 170. The conductive wires, in turn, are electrically coupled to electrical connectors (e.g., "Bal-Seal" connectors) within connector portion 171 of extension component 170. The terminals of one or more stimulation leads 110 are inserted within connector portion 171 for electrical connection with respective connectors. Thereby, the pulses originating from IPG 150 and conducted through the conductors of lead body 172 are provided to stimulation lead 110. The pulses are then conducted through the conductors of lead 110 and applied to tissue of a patient via electrodes 111. Any suitable known or later developed design may be employed for connector portion 171.

For implementation of the components within IPG 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within IPG 150. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may include a lead body of insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number and type of electrodes 111, terminals, and internal conductors.

Controller device 160 may be implemented to recharge battery 153 of IPG 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller device 160 generates an AC-signal to drive current through coil 166 of wand 165. Assuming that primary coil 166 and secondary coil are suitably positioned relative to each other, the secondary coil is disposed within the magnetic field generated by the current driven through primary coil 166. Current is then induced by a magnetic field in the secondary coil. The current induced in the coil of the implantable pulse generator is rectified and regulated to recharge the battery of IPG 150. The charging circuitry may also communicate status messages to controller device 160 during charging operations using pulse-loading or any other suitable technique. For example, controller device 160 may communicate the coupling status, charging status, charge completion status, etc.

External controller device 160 is also a device that permits the operations of IPG 150 to be controlled by a user after IPG 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 150.

Controller device 160 preferably provides one or more user interfaces to allow the user to operate IPG 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. In the methods and systems described herein, stimulation parameters may include, for example, a number of pulses in a burst (e.g., 3, 4, or 5 pulses per burst), an intra-burst frequency (e.g., 500 Hz), an inter-burst frequency (e.g., 40 Hz), and a delay between the pulses in a burst (e.g., less than 1 millisecond (ms)).

IPG 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 2001/093953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference. Example commercially available neurostimulation systems include the EON MINI™ pulse generator and RAPID PROGRAMMER™ device from Abbott Laboratories.

The systems and methods describe herein facilitate generating pulsed waveforms that approximate colored noise for use in a neurostimulation system. A neurostimulation system includes a stimulation lead including a plurality of contacts, and a pulse generator communicatively coupled to the stimulation lead. The pulse generator is configured to generate a pulsed waveform that approximates colored noise using at least one of a thresholding method and an optimization method, and cause stimulation to be delivered by the stimulation lead based on the pulsed waveform.

The stimulation waveforms described herein include a sequence of pulses whose power spectral density (PSD) generally approximates that of colored noise (e.g., pink or brown noise). The pulses in the waveform have a limited maximum pulse width to reduce the accumulation of substances and electrode corrosion. Two example methods of generating pulsed waveforms are described herein—a thresholding method and an optimization method.

Although pink noise and brown noise are given as examples herein, those of skill in the art will appreciate that the systems and methods described herein may be used to generate waveforms that generally approximate any suitable colored noise. That is, the embodiments described herein may be used to generate waveforms that approximate colored noise having a power spectrum that follows $1/f^\alpha$, where a is greater than zero. This includes, for example, $\alpha=1$ (pink noise), $\alpha=2$ (brown noise), and other values of a (including non-integer values).

In the thresholding method, thresholding is applied to a colored noise spectrum, and anodic and cathodic pulses are assigned based on the polarity of the noise after thresholding. In the optimization method, the stimulation waveform is generated using a cost function that represents the error between the PSD of colored noise and a pulse noise waveform.

Applying stimulation using the waveforms described herein may assist patients with abnormal PSD, such as Parkinson's patient with increased beta band oscillation. Further, the physiologically inspired waveforms described herein may be more effective than existing waveforms at treating neurological disorders and chronic pain by restoring neuronal activity to normal states.

Figure 2:
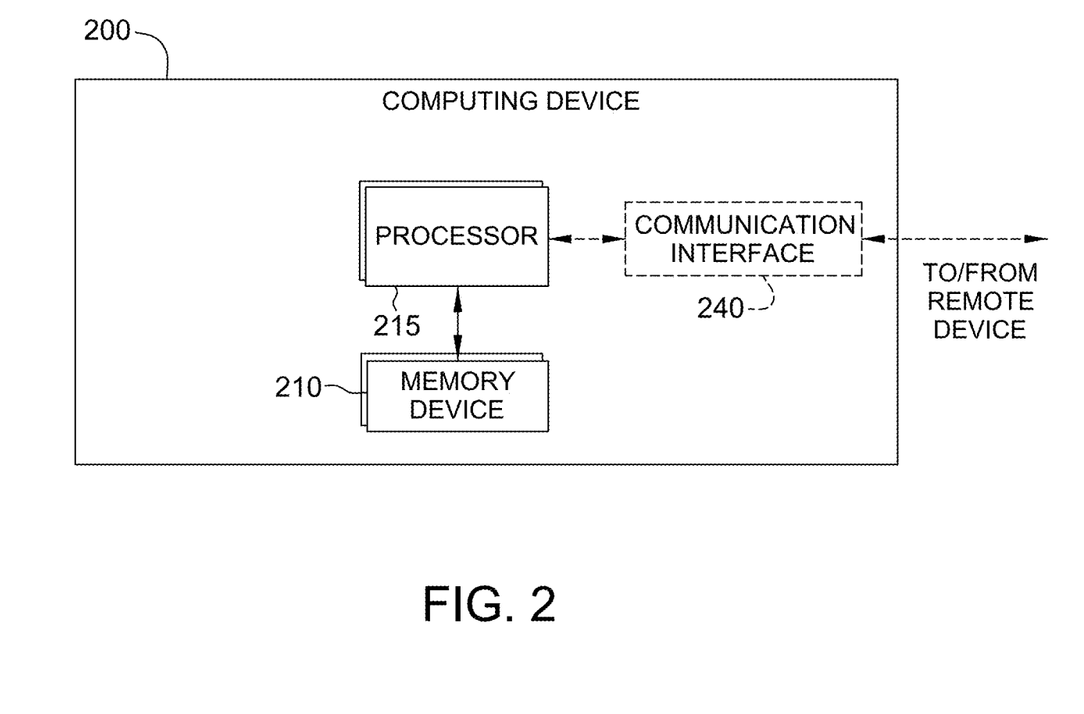
FIG. 2 is a block diagram of one embodiment of a computing device that may be used to generate pulsed waveforms that approximate colored noise.

FIG. 2 is a block diagram of one embodiment of a computing device 200 that may be used to generate pulsed waveforms that approximate colored noise, as described herein. Computing device 200 may be included, for example, within an IPG (e.g., IPG 150) or an external pulse generator.

In this embodiment, computing device 200 includes at least one memory device 210 and a processor 215 that is coupled to memory device 210 for executing instructions. In some embodiments, executable instructions are stored in memory device 210. In the illustrated embodiment, computing device 200 performs one or more operations described herein by programming processor 215. For example, processor 215 may be programmed by encoding an operation as one or more executable instructions and by providing the executable instructions in memory device 210.

Processor 215 may include one or more processing units (e.g., in a multi-core configuration). Further, processor 215 may be implemented using one or more heterogeneous processor systems in which a main processor is present with secondary processors on a single chip. In another illustrative example, processor 215 may be a symmetric multi-processor system containing multiple processors of the same type. Further, processor 215 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein.

In the illustrated embodiment, memory device 210 is one or more devices that enable information such as executable instructions and/or other data to be stored and retrieved. Memory device 210 may include one or more computer readable media, such as, without limitation, dynamic random access memory (DRAM), read-only memory (ROM), electrically erasable programmable read-only memory (EEPROM), static random access memory (SRAM), a solid state disk, and/or a hard disk. Memory device 210 may be configured to store, without limitation, application source code, application object code, source code portions of interest, object code portions of interest, configuration data, execution events and/or any other type of data.

Computing device 200, in the illustrated embodiment, includes a communication interface 240 coupled to processor 215. Communication interface 240 communicates with one or more remote devices, such as a clinician or patient programmer. To communicate with remote devices, communication interface 240 may include, for example, a wired network adapter, a wireless network adapter, a radio-frequency (RF) adapter, and/or a mobile telecommunications adapter.

Figure 3:
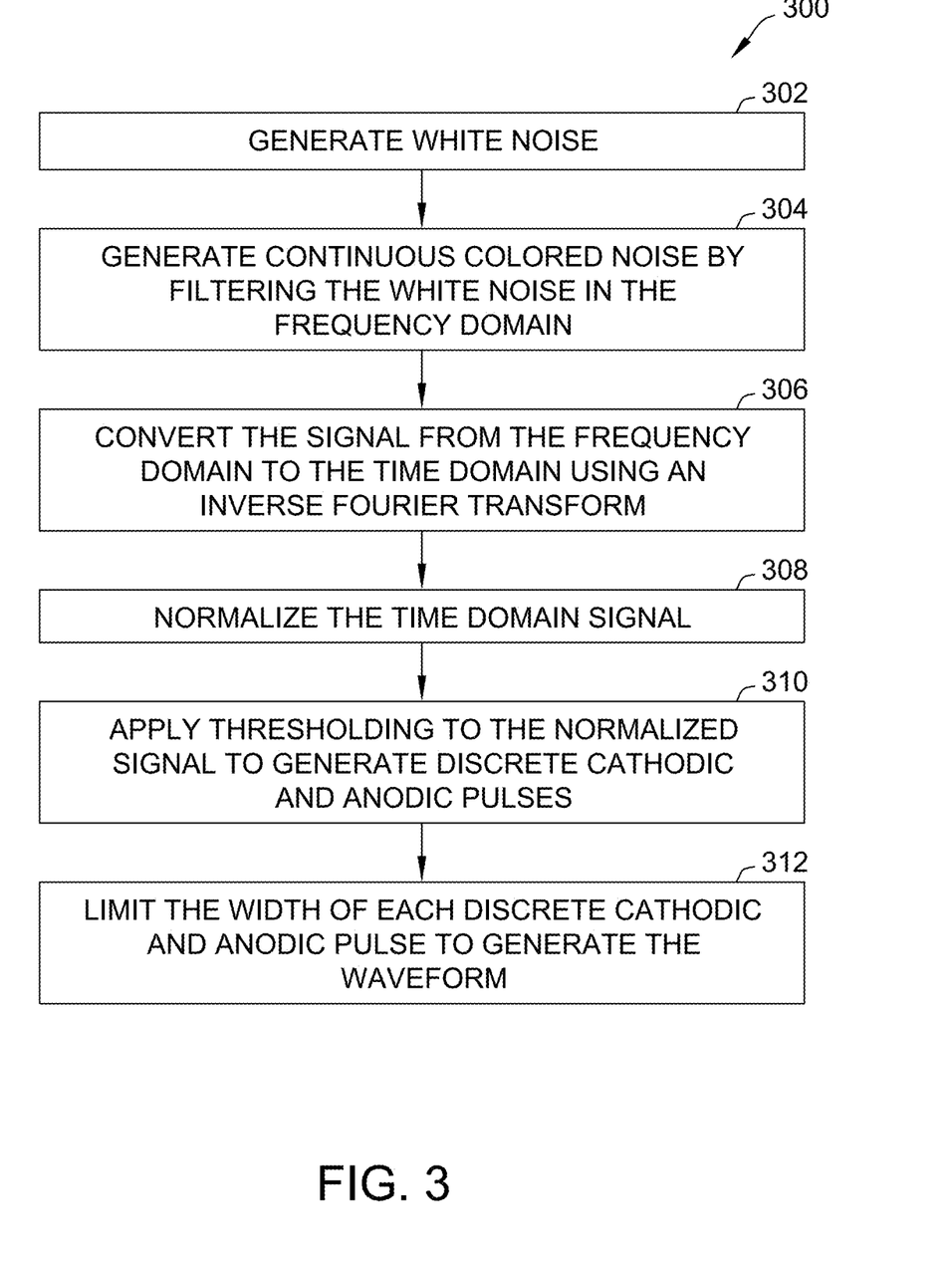
FIG. 3 is a flow chart of one embodiment of a thresholding method for generating pulsed waveforms that approximate colored noise.

FIG. 3 is a flow chart of one embodiment of a thresholding method 300 for generating pulsed waveforms that approximate colored noise. Method 300 may be performed, for example, using computing device 200 (shown in FIG. 2).

At block 302, white noise is generated. White noise may be generated, for example, by generating a set of random numbers of equal probability over a predefined range and resolution. For example, white noise may be generated using a predefined range of −2048 to 2047 and sampling at 10,000 samples per second.

Figure 4:
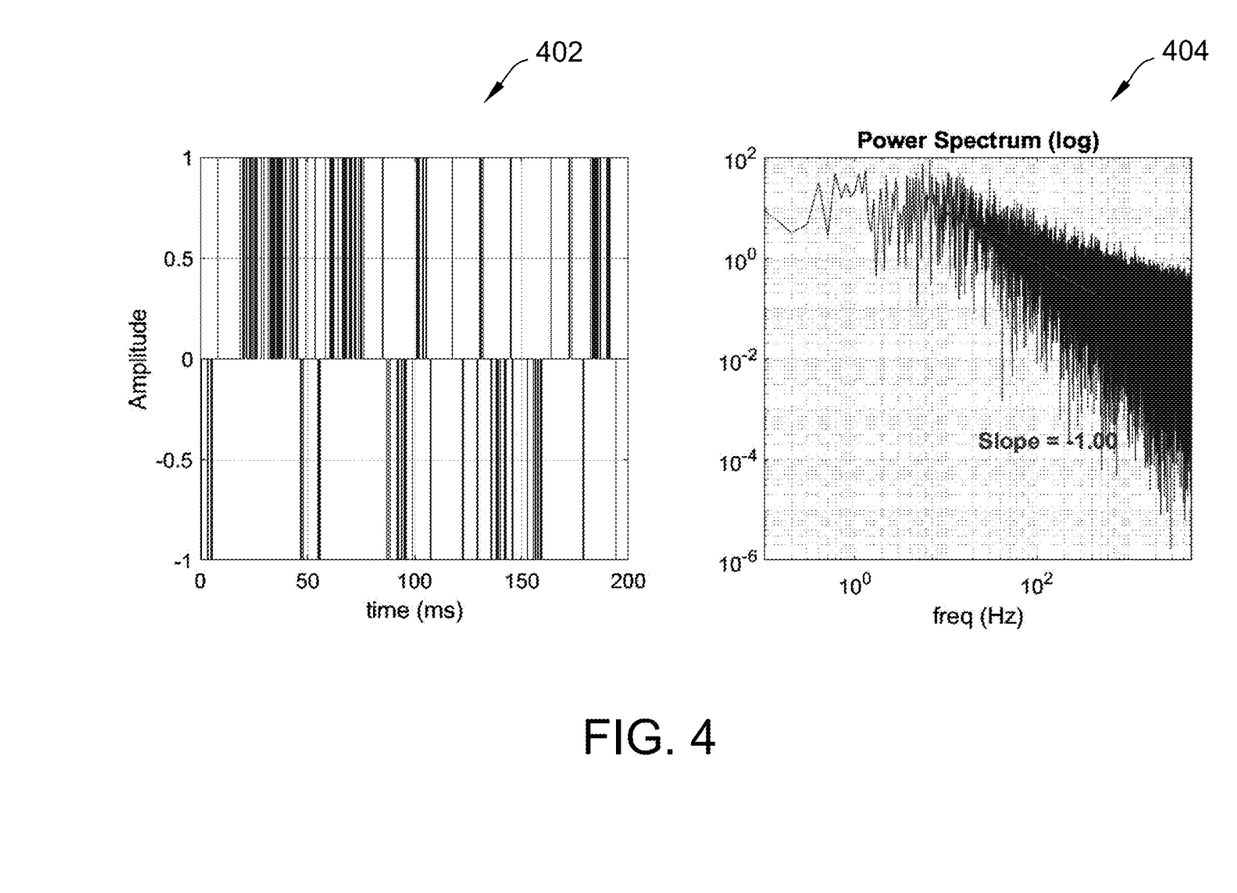
FIG. 4 is a diagram including graphs that demonstrate the thresholding method shown in FIG. 3.

At block 304, the white noise is filtered in the frequency domain to generate continuous colored noise (e.g., pink or brown noise). Then, at block 306, the continuous colored noise is converted from the frequency domain to the time domain using an inverse Fourier transform. In some embodiments, filtering is applied such that the power spectral density remains constant below a predetermined frequency, and the $1/f^\alpha$ ($\alpha > 0$) behavior occurs only above that predetermined frequency. In addition, a high pass filter may be applied to filter out a DC component (i.e., f=0). This is illustrated in FIG. 4 (discussed below).

At block 308, the time domain signal is normalized (e.g., to [−1, 1]). Further, at block 310, a predetermined threshold ($\alpha$) is applied to the normalized signal (x(t)) to generate discrete cathodic and anodic pulses.

For example, in one embodiment, $\alpha$ is greater than zero and less than 1. Then, for the normalized signal, all values that are smaller than the threshold (i.e., |x(t)|<θ) are set to zero. Further, values more positive than the threshold (i.e., x(t)>θ) are set to 1, and values more negative than the inverse of the threshold (i.e., x(t)<−θ) are set to −1. This generates a series of discrete anodic and cathodic pulses.

After the discrete anodic and cathodic pulses are generated, at block 312, the pulse width of each pulse is limited to a predefined maximum pulse width ($T_{PW}$). That is, any pulse having a width greater than $T_{PW}$ is adjusted to have a pulse width equal to $T_{PW}$.

FIG. 4 shows graphs that demonstrate the thresholding method. A first graph 402 shows the discrete anodic and cathodic pulses in the time domain generated after the thresholding of block 310, and a second graph 404 shows the power spectrum for the discrete anodic and cathodic pulses In the frequency domain. Second graph 404 demonstrates that the resulting discrete anodic and cathodic pulses provide a good approximation of a continuous colored noise spectrum (e.g., a 1/f power spectrum for pink noise).

Figure 5:
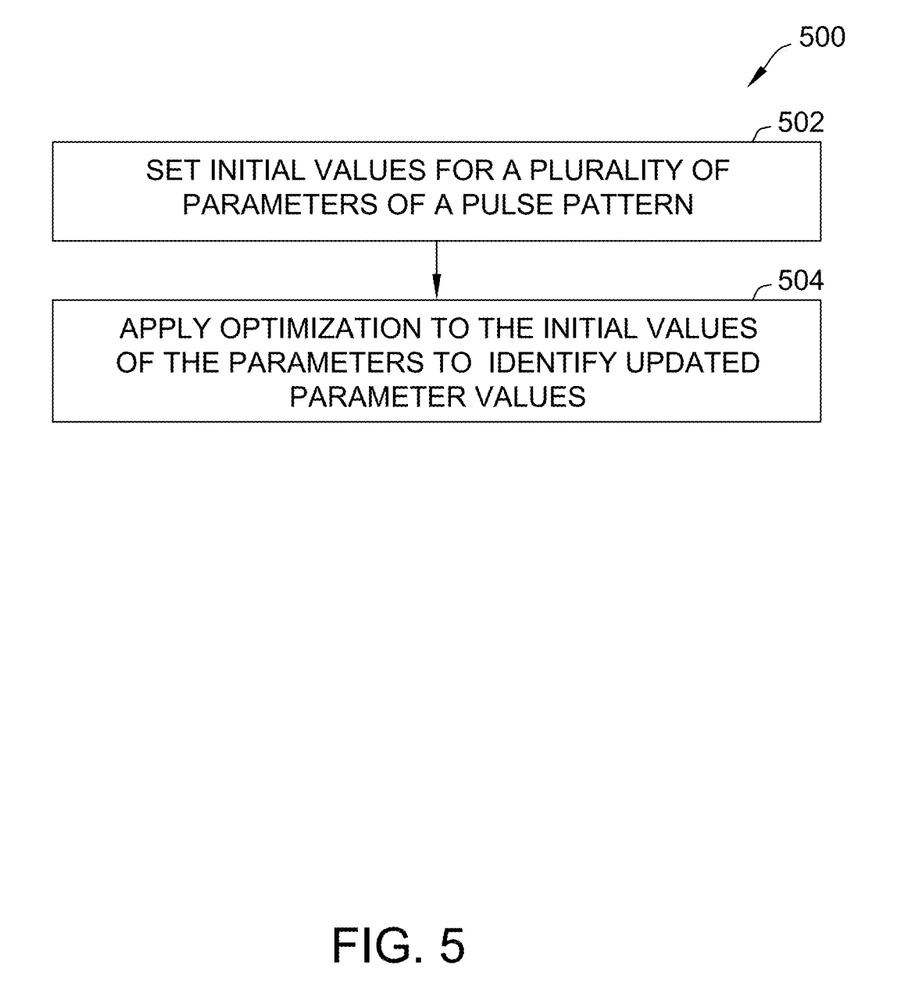
FIG. 5 is a flow chart of one embodiment of an optimization method for generating pulsed waveforms that approximate colored noise.

FIG. 5 is a flow chart of one embodiment of an optimization method 500 for generating pulsed waveforms that approximate colored noise. Method 500 may be performed, for example, using computing device 200 (shown in FIG. 2).

In method 500, an optimization technique is used to identify charge balanced biphasic pulse patterns whose power spectral densities resemble that of colored noise for given frequency bands.

In method 500, a pulse pattern is defined by a plurality of parameters. The parameters may include, for example, i) polarity of the leading pulse (e.g., anodic or cathodic), ii) pulse width, iii) pulse amplitude, iv) the number of pulses per second, and v) pulse timing. Those of skill in the art will appreciate that other variables may be used additionally or alternatively.

At block 502, initial values are set for each of the parameters of the pulse pattern. The parameter values may be set randomly, or may be set to values thought to be associated with pulse patterns that closely approximately colored noise. Alternatively, the parameter values may be set using any suitable method.

Subsequently, at block 504, optimization is applied to the initial values of the parameters to identify updated parameter values (modifying the parameter values of the pulse pattern accordingly) that cause the pulse pattern to approximate colored noise. Applying optimization may include, for example, using a local optimization method such as conjugate gradient descent with initial parameter values adopted from expected best known values, or using a global optimization method such as simulated annealing with initial parameter values set randomly. Heuristic optimization methods such as particle swarm optimization may also be used. Alternatively, any suitable optimization methods may be used.

In one embodiment, the cost function of the optimization is the error between a target power spectral density (e.g., 1/f for pink noise, $1/f^2$ for brown noise) and the power spectral density of the noise corresponding to the pulse pattern. Accordingly, the applied optimization facilitates reducing the error between the target power spectral density and the power spectral density of the noise corresponding to the pulse pattern.

As noted above, the physiologically inspired pulsed noise waveforms described herein may be more effective than at least some known waveforms in treating neurological disorders and chronic pain by restoring abnormal neuronal activity to a normal state.

The embodiments described herein provide systems and methods for generating pulsed waveforms that approximate colored noise for use in a neurostimulation system. An implantable neurostimulation system includes an implantable stimulation lead including a plurality of contacts, and an implantable pulse generator communicatively coupled to the stimulation lead. The pulse generator is configured to generate a pulsed waveform that approximates colored noise using at least one of a thresholding method and an optimization method, and cause stimulation to be delivered by the stimulation lead based on the pulsed waveform.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An implantable neurostimulation system comprising:
    an implantable stimulation lead comprising a plurality of contacts; and
    an implantable pulse generator communicatively coupled to the stimulation lead and configured to:
        generate, using a processor, a pulsed waveform that approximates colored noise by:
            filtering white noise in the frequency domain to generate a continuous colored noise signal;
            converting the continuous colored noise signal to the time domain;
            normalizing the time domain signal;
            applying thresholding to the normalized signal to generate discrete cathodic and anodic pulses, wherein a first subset of the discrete cathodic and anodic pulses have pulse widths greater than a predefined pulse width value, and wherein a second subset of the discrete cathodic and anodic pulses have pulse widths less than the predefined pulse width value; and
            limiting a pulse width of each discrete cathodic and anodic pulse to a predefined maximum pulse width that is equal to the predefined pulse width value by i) reducing the pulse widths of the first subset of the discrete cathodic and anodic pulses to the predefined maximum pulse width and ii) maintaining the pulse widths of the second subset of the discrete cathodic and anodic pulses; and
        cause stimulation to be delivered by the stimulation lead based on the pulsed waveform.

2. The implantable neurostimulation system of claim 1, wherein to filter white noise in the frequency domain to generate the continuous colored noise signal, the implantable pulse generator is configured to filter white noise to generate a continuous pink noise signal.

3. The implantable neurostimulation system of claim 1, wherein to filter white noise in the frequency domain to generate the continuous colored noise signal, the implantable pulse generator is configured to filter white noise to generate a continuous brown noise signal.

4. The implantable neurostimulation system of claim 1, wherein all values in the normalized signal fall between an upper limit and a lower limit, and wherein to apply thresholding, the processor is configured to:
    set values more positive than a non-zero threshold equal to the upper limit;
    set values more negative than an inverse of the non-zero threshold equal to the lower limit; and
    set all other values to zero.

5. The implantable neurostimulation system of claim 1, wherein filtering white noise in the frequency domain comprises applying filtering such that a power spectral density of the continuous colored noise signal remains constant below a predetermined frequency.

6. An implantable pulse generator comprising:
    a memory device; and
    a processor coupled to the memory device, the processor configured to generate a pulsed waveform that approximates colored noise by:
        filtering white noise in the frequency domain to generate a continuous colored noise signal;
        converting the continuous colored noise signal to the time domain;
        normalizing the time domain signal;
        applying thresholding to the normalized signal to generate discrete cathodic and anodic pulses, wherein a first subset of the discrete cathodic and anodic pulses have pulse widths greater than a predefined pulse width value, and wherein a second subset of the discrete cathodic and anodic pulses have pulse widths less than the predefined pulse width value; and
        limiting a pulse width of each discrete cathodic and anodic pulse to a predefined maximum pulse width that is equal to the predefined pulse width value by i) reducing the pulse widths of the first subset of the discrete cathodic and anodic pulses to the predefined maximum pulse width and ii) maintaining the pulse widths of the second subset of the discrete cathodic and anodic pulses.

7. The implantable pulse generator of claim 6, wherein to filter white noise in the frequency domain to generate the continuous colored noise signal, the processor is configured to filter white noise to generate a continuous pink noise signal.

8. The implantable pulse generator of claim 6, wherein to filter white noise in the frequency domain to generate the continuous colored noise signal, the processor is configured to filter white noise to generate a continuous brown noise signal.

9. A method of applying neurostimulation, the method comprising:
    generating, using a processor of an implantable pulse generator, a pulsed waveform that approximates colored noise by:
        filtering white noise in the frequency domain to generate a continuous colored noise signal;
        converting the continuous colored noise signal to the time domain;
        normalizing the time domain signal;
        applying thresholding to the normalized signal to generate discrete cathodic and anodic pulses, wherein a first subset of the discrete cathodic and anodic pulses have pulse widths greater than a predefined pulse width value, and wherein a second subset of the discrete cathodic and anodic pulses have pulse widths less than the predefined pulse width value; and
        limiting a pulse width of each discrete cathodic and anodic pulse to a predefined maximum pulse width that is equal to the predefined pulse width value by i) reducing the pulse widths of the first subset of the discrete cathodic and anodic pulses to the predefined maximum pulse width and ii) maintaining the pulse widths of the second subset of the discrete cathodic and anodic pulses; and applying the waveform to a patient using an implantable stimulation lead coupled to the implantable pulse generator.

10. The method of claim 9, wherein filtering white noise in the frequency domain to generate the continuous colored noise signal comprises filtering white noise to generate one of a continuous pink noise signal and a continuous brown noise signal.

\* \* \* \* \*